United States Patent [19]
Patterson

[11] Patent Number: 5,391,152
[45] Date of Patent: Feb. 21, 1995

[54] CATHETER INTERLOCK ASSEMBLY

[75] Inventor: Frank V. Patterson, Exeter, N.H.

[73] Assignee: C. R. Bard, Inc., Murray Hill, N.J.

[21] Appl. No.: 30,991

[22] Filed: Mar. 12, 1993

[51] Int. Cl.⁶ ............................................. A61M 25/00
[52] U.S. Cl. ...................................... 604/165; 604/280
[58] Field of Search ......................... 604/165, 164, 280

[56] References Cited

U.S. PATENT DOCUMENTS

| | | | |
|---|---|---|---|
| 3,459,183 | 8/1969 | Ring et al. | 604/165 |
| 3,860,006 | 1/1975 | Patel | 128/347 |
| 4,192,305 | 3/1980 | Seberg | 128/214.4 |
| 4,230,123 | 10/1980 | Hawkins, Jr. | 604/165 |
| 4,362,156 | 12/1982 | Feller, Jr. et al. | 604/165 |
| 4,609,370 | 9/1986 | Morrison | 604/165 |
| 4,682,981 | 7/1987 | Suzuki et al. | 604/158 |
| 4,793,363 | 12/1988 | Ausherman et al. | 604/165 |
| 4,946,443 | 8/1990 | Hauser et al. | 604/165 |
| 4,986,814 | 1/1991 | Burney et al. | 604/164 |
| 5,104,382 | 4/1992 | Brinkerhoff et al. | 604/165 |
| 5,205,828 | 4/1993 | Kedem | 604/165 |
| 5,250,036 | 10/1993 | Farivar | 604/165 |

*Primary Examiner*—Paul J. Hirsch
*Attorney, Agent, or Firm*—Morgan & Finnegan

[57] ABSTRACT

A catheter assembly comprising two elements each of which have a hub disposed at the proximal end thereof. The hubs are constructed so as to be complementary and rotatably engageable. When the hubs are engaged, the complementary construction of the hubs secures the axial alignment of the engaged hubs and inhibits an accidental rotational disengagement of the hubs.

57 Claims, 5 Drawing Sheets

CATHETER INTERLOCK ASSEMBLY

BACKGROUND OF THE INVENTION

The invention relates to medical devices for introducing catheters or the like into blood vessels of the body.

Catheter introducers provide a reusable conduit for the passage of catheters and other medical devices, e.g., guidewires, through the body flesh into blood vessels or other body passageways. The catheter introducer is initially inserted into the blood vessel through the use of an introducer assembly.

Introducer assemblies are well known in the prior art. U.S. Pat. No. 5,098,392 granted to K. Amplatz et al. on Mar. 24, 1992 discloses such an introducer assembly comprising (1) an introducer element consisting of an elongated tubular member defining an introducer sheath and an introducer hub disposed at the proximal end of the introducer sheath which further defines an introducer conduit along a longitudinal axis, and (2) a dilation element consisting of an elongated tubular member defining a dilator having a tapered distal end portion and a dilator hub disposed at the proximal end of the dilator, which is sized so that the dilator may be inserted through the conduit of the introducer hub and introducer sheath and that the dilator tapered distal portion extends beyond the introducer sheath distal end.

Prior to the use of the introducer assembly, a needle is inserted through the body flesh and into a blood vessel, and a guidewire is inserted into the blood vessel through the center passage of the needle. The needle is then removed leaving the guidewire in place. The introducer assembly is then inserted over the guidewire such that the tapered distal portion of the dilator acts to gradually expand the puncture opening to ease the passage of the introducer sheath into the blood vessel. After the introducer sheath has been inserted to a desired depth within the blood vessel, the dilator element is removed from within the introducer element.

During the initial insertion of the introducer assembly, the body's resistance to the expansion of the puncture opening exerts forces on the distal portion of the dilator tending to push the dilator distal end rearwardly in the proximal direction into the introducer sheath. In order to ensure that the tapered distal portion of the dilator remains extended beyond the blunt distal end of the introducer sheath during the initial insertion of the introducer assembly, the dilator hub is releasably connected to the introducer hub.

In addition to introducer/dilator assemblies, other catheter assemblies include the combination of an introducer sheath with obturators, sterile sleeves, Tuohy-Borst fittings and the like.

Several means for releasably connecting the introducer hub and the hub of the other component of the assembly, e.g. the dilator hub, are known in the prior art. Unfortunately, with these prior art designs, the interconnected hubs are prone to becoming accidently disengaged.

A prior art means for releasably connecting the dilator hub and introducer hub comprises rotatably engaging studs and complementary slots associated with the dilator and introducer hubs. Seberg U.S. Pat. No. 4,192,305 discloses a catheter placement assembly having a needle and lumen wherein the needle and lumen are mechanically engaged by complementary means associated with the needle and lumen hubs, such as tabs associated with one hub and slots associated with the other hub. U.S. Pat. No. 4,946,443 granted to L. Hauser et al. on Aug. 7, 1990 discloses a catheter assembly having a releasable connecting means consisting of a pin or stud associated with one hub that is received by a slot associated with the other hub. Medical assemblies having releasable connecting means of the pin-and-slot type are also disclosed in Morrison U.S. Pat. No. 4,609,370; Burney et al. U.S. Pat. No. 4,986,814; and Patel U.S. Pat. No. 3,860,006. These types of rotatably engaging releasable connecting means do not have a stop means for securely locking the pin within the slot and, therefore, are prone to accidental disengagement through the inadvertent rotation of the dilator hub.

Other prior art releasable connecting means do not suggest a means for inhibiting the rotational disengagement of the introducer and dilator hubs. For instance, Amplatz et al. U.S. Pat. No. 5,098,393 discloses that the dilator hub and introducer hub may be releasably connected by an axially engaging snap fit or friction fit connection. An axially aligned snap fit connection of the type disclosed in Amplatz et al. U.S. Pat. No. 5,098,393 is prone to accidental disengagement through the inadvertent application of a transverse force to the proximal end of the dilator hub. Moreover, while the axial alignment of the dilator and introducer hubs is maintained with such a releasable connection, rotational movement between the dilator and introducer hubs is permitted.

Upon an accidental disengagement of the dilator hub and introducer hub during the initial insertion of the introducer assembly, the tapered distal end of dilator would migrate proximally into the introducer sheath and the blunt distal end of the introducer sheath may be forced into the blood vessel. In that event, trauma to the blood vessel and body flesh surrounding the puncture site could result. Such trauma may result in the procedure being re-initiated at another location along the blood vessel or being abandoned altogether. Accidental disengagement of an obturator can result in kinking of the introducer sheath thus preventing further use of the sheath and requiring replacement with a new sheath. Similarly, disengagement of a sterile sleeve from the introducer sheath will compromise the required sterile environment. Further, disengagement of the Tuohy-Borst fitting from the introducer sheath can cause the catheter, which is received by the fitting and within the introducer, to move from its desired position in the patient.

Accordingly, it is an object of the present invention to provide a catheter assembly with an improved rotatably engaging releasable interlock connection between the hubs of the assembly components which minimizes, or preferably eliminates, the risk of accidental disengagement of both the axial and rotational alignment of the hubs.

SUMMARY OF THE INVENTION

The present invention resides in the improvement of the rotatably engaging releasable interlock connection between the component hubs of a catheter assembly such as between a dilator hub and an introducer hub. The introducer assembly with improved releasable interlock connection comprises a first element having a hub with outwardly protruding radial tabs disposed at the distal end of the hub and a second element having a hub with two complementary slots and two interference fit protuberances disposed at the proximal portion of the second element hub which rotatably receive and secure the first element tabs. An alternative embodiment of the releasable interlock connection comprises axially disposed pins and complementary slots wherein the slots are sized to provide an interference fit between the pins and slots.

BRIEF DESCRIPTION OF THE DRAWINGS

The invention will be further described, by way of example, with reference to the accompanying drawings; wherein.

DETAILED DESCRIPTION OF THE PREFERRED EMBODIMENTS

It should be noted that while the following description will be specifically in the context of an introducer/dilator assembly, the invention is not so limited and is applicable to other catheter assemblies.

Figure 1:
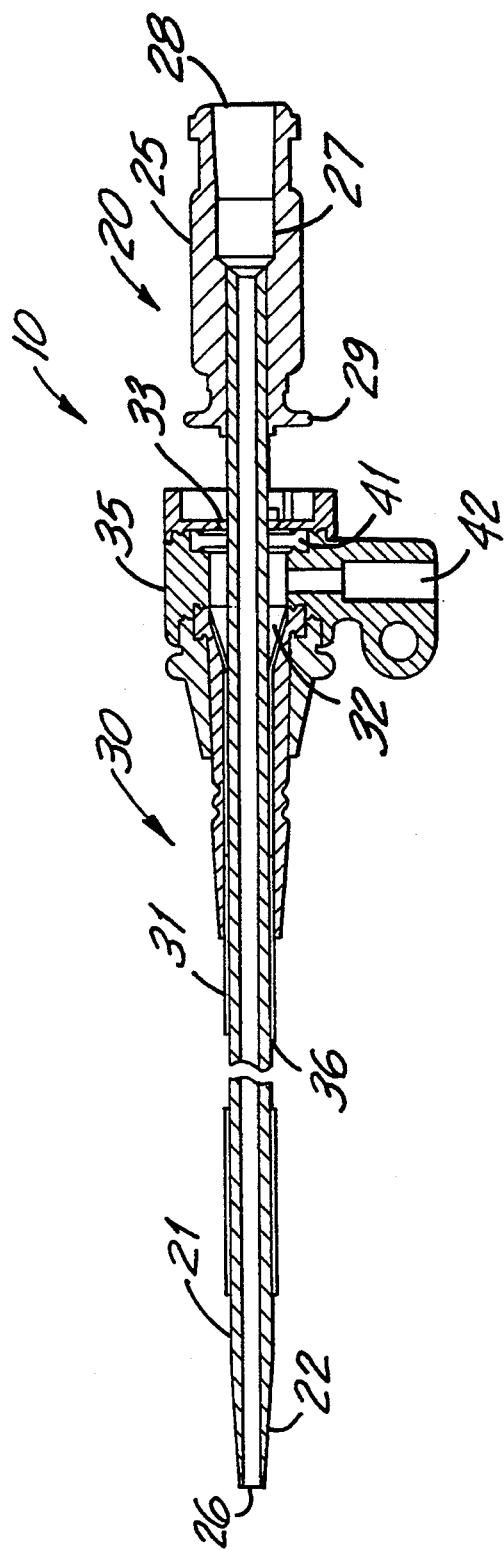
FIG. 1 is a cross-sectional view of the introducer assembly of the invention.

Referring to FIG. 1, assembly 10 comprises a dilator element 20 having a dilator hub 25 and an introducer element 30 having an introducer hub 35. As will be described below, the dilator hub 25 and introducer hub 35 may be mechanically interlocked.

The dilator element 20 comprises a dilator 21 with a tapered distal portion 22 and a longitudinal dilator conduit 26 defining a longitudinal axis. Preferably, dilator 21 is formed of a semi-rigid polymer, such as polyvinyl chloride, polypropylene, polyethylene, polyethylene terephthalate, polyurethane, Teflon or Nylon. The dilator hub 25 is disposed at the proximal end of the dilator 21 and includes a bore 27 and a port 28 which communicate with dilator conduit 26. Preferably, the dilator hub 25 is formed of a rigid polymer, such as polyethylene or acrylonitrile butadiene styrene (ABS).

Figure 3:
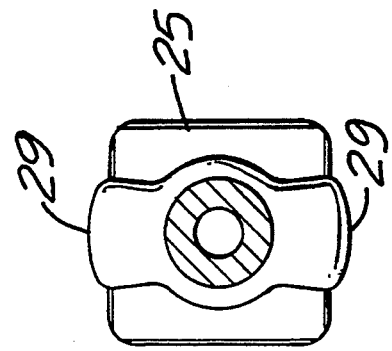
FIG. 3 is a side-elevational view of the dilator hub when viewed along line 3—3 of FIG. 2.
Figure 2:
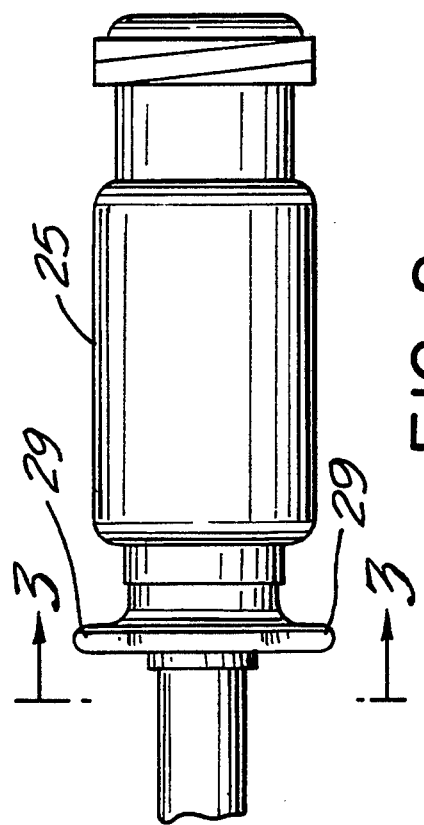
FIG. 2 is a front-elevational view of the dilator hub portion of the invention.

Referring to FIGS. 2 and 3, in a preferred embodiment, two radially outward protruding tabs 29 are disposed at the distal end of the dilator hub 25. The tabs 29 may be formed of the same material as dilator hub 25.

The tabs 29 may be of unitary construction with dilator hub 25 or attached thereto in an integral fashion.

The introducer element 30 comprises an introducer sheath 31 having a longitudinal introducer conduit 36. Typically, the distal end of the introducer sheath 31 is tapered, but it may be blunt. Preferably, introducer sheath 31 is formed of a semi-rigid polymer, such as polyvinyl chloride, polypropylene, polyethylene, polyethylene terephthalate, polyurethane, Teflon or Nylon. The introducer hub 35 is affixed to the proximal end of the introducer sheath 31 and includes a bore 32 and port 33 which communicate with introducer conduit 36. Preferably, the introducer hub 35 is formed of a rigid polymer, such as polyethylene or ABS.

The introducer hub 35 comprises a hemostasis valve 41 and a sidearm infusion leg 42. The hemostasis valve 41 limits the leakage of blood through the introducer element 30. The construction and operation of hemostasis valve 41 is well known in the art. See Amplatz et al. U.S. Pat. No. 5,098,393. A tube and stopcock (NOT SHOWN IN FIGURES) may be connected to the sidearm infusion leg 42. If required, heparin or other chemicals may be directly administered into the blood vessel through the sidearm infusion leg 42.

Figure 4:
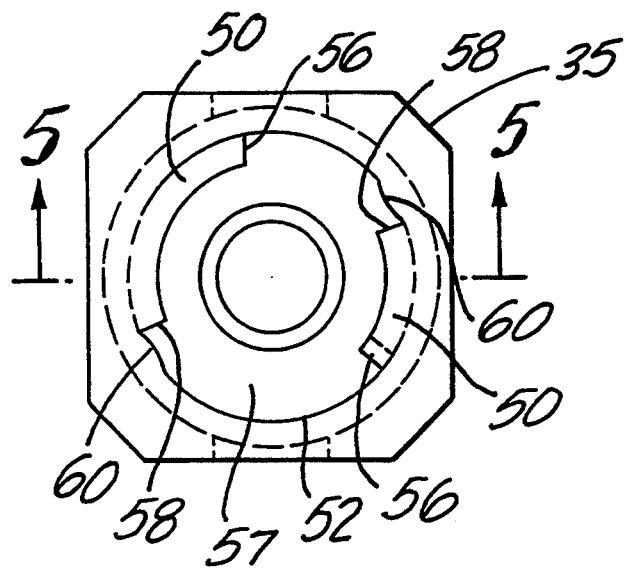
FIG. 4 is a cross-sectional view of the proximal end of the introducer hub portion of the invention.
Figure 5:
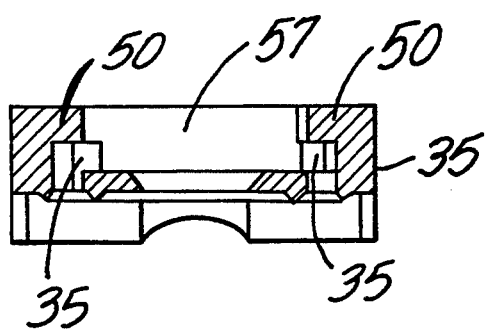
FIG. 5 is a cross-sectional view of the proximal end of the introducer hub when viewed along line 5—5 in FIG. 4.

Referring to FIGS. 4 and 5, in a preferred embodiment, a cylindrical recess 57 is disposed at the proximal end of the introducer hub 35. Two projections 50 disposed on the circumferential surface 52 of cylindrical recess 57 form two slots 55, each having an open end 58 and a closed end 56. Each slot 55 extends circumferentially within cylindrical recess 57 through an arc of from about 50° to about 90°.

The dilator hub 25 and introducer hub 35 may be mechanically interlocked by inserting tabs 29 into the cylindrical recess 57 and rotating the dilator hub 25 until tabs 29 are engaged within slots 55 through open end 58 and further rotation is precluded by closed end 56 of slots 55. Thus, closed end 56 of slots 55 define a first stop to inhibit the rotational disengagement of tabs 29 from slots 55 in one circumferential direction (as shown in FIG. 4, the clockwise direction). Protuberances 60 are provided to define a second stop to inhibit the accidental rotational disengagement of tabs 29 from slots 55 in the opposite circumferential direction (as shown in FIG. 4, the counter-clockwise direction).

More specifically, two protuberances 60 are disposed on the circumferential surface 52 of the cylindrical recess 57, each in the proximity of the open end 58 of slot 55 such that the circumferential distance between protuberance 60 and the open end of slot 55 is less than the width of tabs 29. Protuberances 60 are sized so that there is an interference fit between protuberances 60 and tabs 29 when tabs 29 are rotated into open end 58 of slots 55 such that protuberances 60 provide resistance to the rotation of tabs 29 but do not prevent the rotation of tabs 29 into slots 55. After tabs 29 have been rotated past protuberances 60 and have been engaged in slots 55, protuberances 60 provide resistance to the disengagement of tabs 29 from slots 55 through open end 58 thereof.

The location of protuberances 60 relative to open end 58 of slots 55 precludes tabs 29 from being disengaged without the resistance posed by protuberances 60 first being overcome. Protuberances 60 and closed end 56 of slots 55 inhibit the rotational disengagement of tabs 29 from slots 55. Projections 50 preclude the axial disengagement of tabs 29 from slots 55.

The user, in overcoming the resistance posed by protuberances 60, is provided with a tactile sense of the introducer hub 35 and the dilator hub 25 being either engaged or disengaged.

Figure 6:
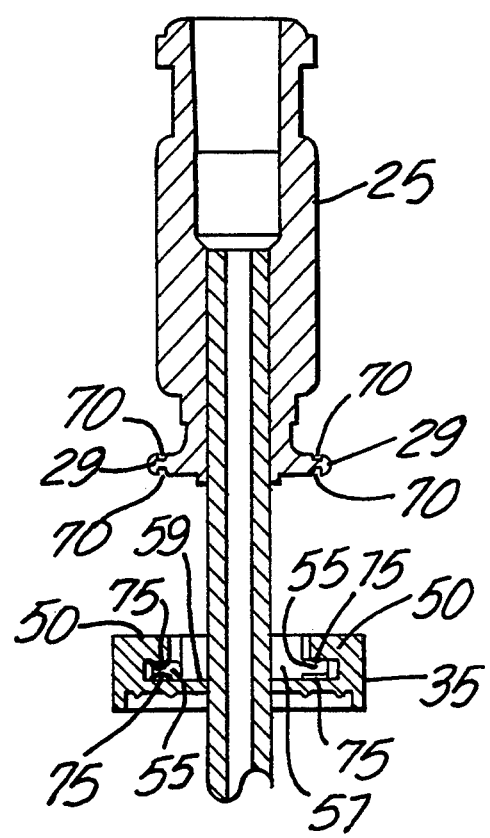
FIG. 6 is a cross-sectional view of the dilator hub and proximal end of the introducer hub of an alternative embodiment of the invention.

FIG. 6 depicts an alternative embodiment of the complementary means associated with the dilator hub 25 and introducer hub 35 for releasably interlocking dilator hub 25 and introducer hub 35 and for providing mechanical resistance to the rotational disengagement of the interlocked dilator hub 25 and introducer hub 35. In this embodiment, a plurality of indentations 70 are deposed on the surfaces of tabs 29. A plurality of protuberances 75 extend circumferentially along projections 50 and surface 59 of cylindrical recess 57 such that slots 55 are complementary to tabs 29 with indentations 70. Protuberances 75 are sized so that there is an inference fit between the protuberances 75 and tabs 29 when tabs 29 are engaged within slot 55. Once tabs 29 are engaged within slots 55, this interference fit and closed end 56 of slots 55 inhibit an accidental rotational disengagement of tabs 29 from slots 55. As is the case in the above described preferred embodiment, axial disengagement of tabs 29 from slots 55 is precluded by projections 50.

Figure 7:
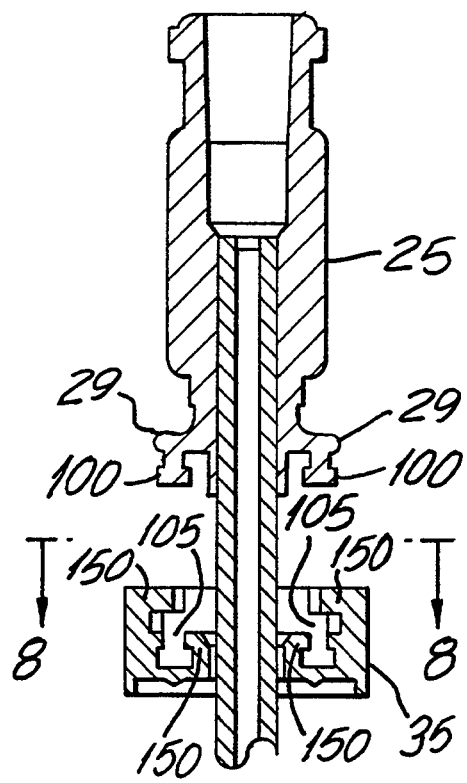
FIG. 7 is a cross-sectional view of the dilator hub and proximal end of the introducer hub of an another alternative embodiment of the invention.
Figure 8:
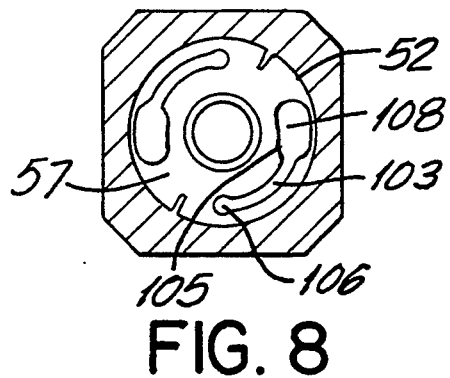
FIG. 8 is a cross-sectional view of the proximal end of the introducer hub when viewed along line 8—8 in FIG. 7.
Figure 9:
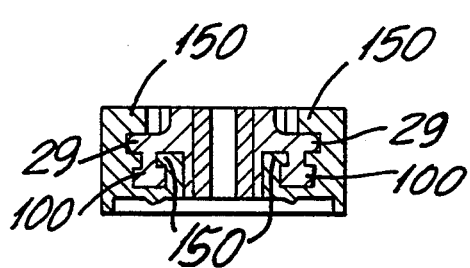
FIG. 9 is a portion of a cross-sectional view of the alternative embodiment depicted in FIG. 7 wherein the dilator and introducer hubs are engaged.

FIGS. 7, 8 and 9 depict another alternative embodiment of the complementary means associated with the dilator hub 25 and introducer hub 35 for releasably interlocking the same and for providing mechanical resistance to the axial and rotational disengagement of the interlocked dilator hub 25 and introducer hub 35. In this embodiment, two pins 100 are axially disposed on the distal end of tabs 29. Projections 150 disposed on circumferential surface 52 of cylindrical recess 57 form slots 105 on the proximal end of the introducer hub 35 that are complementary with tabs 29 and pins 100. As depicted in FIG. 8, each slot 105 extends circumferentially within cylindrical recess 57 through an arc of from about 50° to about 90°.

Slot 105 comprises an enlarged open end 108 for receiving pin 100, an interfering portion 103 of narrow width and a closed end 106. The width of the interfering portion 103 of slot 105 is sized so that there is an interfering fit between slot 105 and tabs 29 with pins 100 when tabs 29 are engaged within slots 105 and rotated through the interfering portion 103.

The dilator hub 25 and introducer hub 35 may be mechanically interlocked by inserting tabs 29 with pins 100 into enlarged open end 108 of slots 105 and rotating tabs 29 through interfering portion 103 until further rotation is precluded by closed end 106 of slots 105. Once tabs 29 with pins 100 are engaged within slots 105, axial disengagement is precluded by projections 150. The closed end 106 and the resistance posed by the interfering portion 103 of slots 105 define two stops which inhibit an accidental rotational disengagement of tabs 29 and pins 100 from slots 105.

Figure 10:
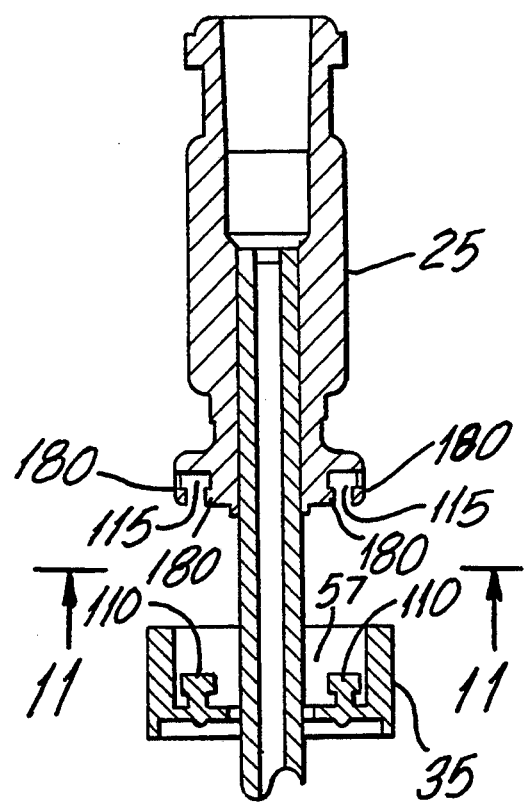
FIG. 10 is a cross-sectional view of the dilator hub and proximal end of the introducer hub of another alternative embodiment of the invention.
Figure 11:
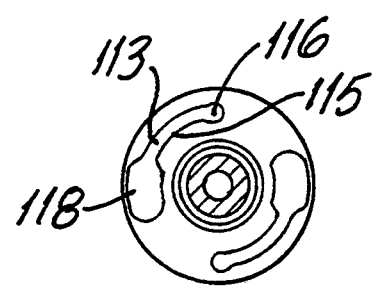
FIG. 11 is a cross-sectional view of the dilator hub when viewed along line 11—11 in FIG. 10.

In a similar alternative embodiment depicted in FIGS. 10 and 11, two pins 110 are disposed within the cylindrical recess 57 of introducer hub 35. Complementary slots 115 are disposed on the distal end of dilator hub 25. Each slot 115 extends circumferentially through an arc of from about 50° to about 90°. Slot 115 comprises an enlarged open end 118 for receiving pin 110, an interfering portion 113 of narrow width, and closed end 116. The width of interfering portion 113 of slots 115 is sized so that there is an interfering fit between slots 115 and pins 110 when pins 110 are engaged within slots 115 and rotated through the interfering portion 113.

The dilator hub 25 and introducer hub 35 may be mechanically interlocked by inserting pins 110 into enlarged open end 118 of slots 115 and rotating pins 110 through interfering portion 113 until further rotation is precluded by closed end 116 of slots 115. Once pins 110 are engaged within slots 115, axial disengagement is precluded by projections 180 formed by slots 115 in the distal end of the dilator hub 25. The closed end 116 and the resistance posed by the interfering portion 113 of slots 115 define two stops which inhibit accidental rotational disengagement.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

What is claimed is:

1. A catheter assembly comprising:
   a first catheter element having a proximal end and a distal end, the first catheter element having a hub disposed at the proximal end thereof;
   a second catheter element having a proximal end and a distal end, the second catheter element having a hub disposed at the proximal end thereof wherein the second catheter element hub is engageable with the first catheter element hub;
   rotatable interlock means complementarily associated with the first catheter element hub and the second catheter hub for rotatably releasably engaging the first catheter element hub and the second catheter element hub in an axial alignment;
   axial securement means for securing the axial alignment of the engaged first catheter element hub and second catheter element hub; and
   rotational securement means for inhibiting a rotational disengagement of the engaged first catheter element hub and second catheter element hub, the rotational securement means is in an interference fit relationship with the rotatable interlock means.

2. The catheter assembly defined in claim 1 wherein the interlock means comprises two radially extending tabs disposed on the distal end of the first catheter element hub and two complementary slots disposed on the proximal end of the second catheter element hub for rotatably receiving the tabs.

3. The catheter assembly defined in claim 2 wherein the axial securement means comprises projections disposed on the proximal end of the second catheter element hub so as to inhibit an axial disengagement of the tabs from the complementary slots.

4. The catheter assembly defined in claim 3 wherein each of the complementary slots terminates in an end wall defining a first stop to inhibit a rotational disengagement of the tabs from the slots and further comprising a protuberance disposed on the proximal end of the second catheter element hub sized so as to provide an interference fit between the protuberance and a tab defining a second stop to inhibit a rotational disengagement of the tabs from the slots, the first and second stops comprise the rotational securement means.

5. The catheter assembly defined in claim 3 wherein each of the complementary slots terminates in an end wall defining a first stop to inhibit a rotational disengagement of the tabs from the slots and further comprising two protuberances disposed on the proximal end of the second catheter element hub sized so as to provide an interference fit between the protuberances and tabs defining a second stop to inhibit a rotational disengagement of the tabs from the slots, the first stop and second stops comprise the rotational securement means.

6. The catheter assembly defined in claim 1 wherein the interlock means comprises two axially aligned pins disposed on the distal end of the first catheter element hub and two complementary slots disposed on the proximal end of the second catheter element hub.

7. The catheter assembly defined in claim 6 wherein the axial securement means are projections disposed on the proximal end of the second catheter element hub so as to inhibit an axial disengagement of the pins from the complementary slots.

8. The catheter assembly defined in claim 7 wherein each of the complementary slots terminates in a closed end defining a first stop to inhibit a rotational disengagement of the pins from the slots and further comprising a second stop comprising an interference fit between a pin and a slot along a portion of the slot, the first stop and second stop comprise the rotational securement means.

9. The catheter assembly defined in claim 7 wherein each of the complementary slots terminates in a closed end defining a first stop to inhibit a rotational disengagement of the pins from the slots and further comprising a second stop comprising an interference fit between the pins and the slots along a portion of each slot, the first stop and second stop comprise the rotational securement means.

10. The catheter assembly defined in claim 1 wherein the interlock means comprises two axially aligned pins disposed on the proximal end of the second catheter element hub and two complementary slots disposed on the distal end of the first catheter element hub.

11. The catheter assembly defined in claim 10 wherein the axial securement means are projections disposed on the distal end of the first catheter element hub so as to inhibit an axial disengagement of the pins from the complementary slots.

12. The catheter assembly defined in claim 11 wherein each of the complementary slots terminates in a closed end defining a first stop to inhibit a rotational disengagement of the pins from the slots and further comprising a second stop comprising an interference fit between a pin and a slot along a portion of the slot, the first stop and second stop comprise the rotational securement means.

13. The catheter assembly defined in claim 11 wherein each of the complementary slots terminates in a closed end defining a first stop to inhibit a rotational disengagement of the pins from the slots and further comprising a second stop comprising an interference fit between the pins and the slots along a portion of each slot, the first and second stop comprise the rotational securement means.

14. The catheter assembly defined in claim 1 wherein the interlock means comprises two radially extending tabs disposed on the distal end of the first catheter element hub having a distal surface and a proximal surface and defining a plurality of indentations on the distal and proximal surfaces of the tabs, and two complementary slots disposed on the proximal end of the second catheter element hub for rotatably receiving the tabs.

15. The catheter assembly defined in claim 14 wherein the axial securement means are projections disposed on the proximal end of the second catheter element hub so as to inhibit an axial disengagement of the tabs from the complementary slots.

16. The catheter assembly defined in claim 15 wherein each of the complementary slots terminates in a closed end defining a first stop to inhibit a rotational disengagement of the tabs from the slots and further comprising a second stop comprising an interference fit between a tab and a slot along a portion of the slot, the first and second stop comprise the rotational securement means.

17. The catheter assembly defined in claim 15 wherein each of the complementary slots terminates in a closed end defining a first stop to inhibit a rotational disengagement of the tabs from the slots and further comprising an interference fit between the tabs and the slots along a portion of each slot, the first and second stop comprise the rotational securement means.

18. A catheter assembly comprising:
an introducer sheath comprising an elongated tubular element having a distal end and a proximal end, the introducer sheath defining an introducer conduit along a longitudinal axis;
an introducer hub having a distal end and proximal end, the introducer hub disposed at the proximal end of the introducer sheath and further defining an introducer conduit therethrough and a cylindrical recess at the proximal end;
a dilator comprising an elongated tubular element having a distal end and a proximal end, the dilator defining a longitudinal dilator conduit, the dilator having a tapered distal portion, the dilator being receivable through the introducer conduit so that the tapered distal portion of the dilator extends beyond the distal end of the introducer sheath;
a dilator hub having a distal end and a proximal end, the dilator hub disposed at the proximal end of the dilator and further defining a dilator conduit therethrough;
two radially extending tabs disposed on the distal end of the dilator hub;
two circumferentially extending projections disposed within the cylindrical recess at the proximal end of the introducer hub so as to form two slots for rotatably receiving the tabs and that terminate in end walls defining a first stop to inhibit a rotational disengagement of the tabs from the slots in a first circumferential direction, the projections further inhibit an axial disengagement of the tabs from the slots; and
two protuberances disposed within the cylindrical recess at the proximal end of the introducer hub, each of the protuberances is sized to provide an interference fit between the protuberance and one of the radially extending tabs so as to define a second stop to inhibit a rotational disengagement of the tabs from the slots in a second circumferential direction.

19. A catheter assembly comprising:
an introducer sheath comprising an elongated tubular element having a distal end and a proximal end, the introducer sheath defining an introducer conduit along a longitudinal axis;
an introducer hub having a distal end and proximal end, the introducer hub disposed at the proximal end of the introducer sheath and further defining an introducer conduit therethrough and a cylindrical recess at the proximal end;
a dilator comprising an elongated tubular element having a distal end and a proximal end, the dilator defining a longitudinal dilator conduit, the dilator having a tapered distal portion, the dilator being receivable through the introducer conduit so that the tapered distal portion of the dilator extends beyond the distal end of the introducer sheath;

a dilator hub having a distal end and a proximal end, the dilator hub disposed at the proximal end of the dilator and further defining a dilator conduit therethrough;

two radially extending tabs disposed on the distal end of the dilator hub having a distal surface and a proximal surface, and defining a plurality of indentations on the distal and proximal surfaces of the tabs;

two circumferentially extending projections disposed within the cylindrical recess at the proximal end of the introducer hub so as to form two circumferentially extending slots for rotatably receiving the tabs that terminate in end walls defining a first stop to inhibit a rotational disengagement of the tabs from the slots in a first circumferential direction, the projections further inhibit an axial disengagement of the tabs from the slots; and a plurality of protuberances extending circumferentially along the projections and circumferentially along a surface of the cylindrical recess in the proximal end of the introducer hub such that the two slots are complementary to the tabs, the protuberances are sized so as to provide an interference fit between the protuberances and the tabs defining a second stop to inhibit a rotational disengagement of the tabs from the slots in a second circumferential direction.

20. A catheter assembly comprising:

an introducer sheath comprising an elongated tubular element having a distal end and a proximal end, the introducer sheath defining an introducer conduit along a longitudinal axis;

a dilator comprising an elongated tubular element having a distal end and a proximal end, the dilator defining a longitudinal dilator conduit, the dilator having a tapered distal portion, the dilator being receivable through the introducer conduit so that the tapered distal portion of the dilator extends beyond the distal end of the introducer sheath;

a dilator hub having a distal end and a proximal end, the dilator hub disposed at the proximal end of the dilator and further defining a dilator conduit therethrough;

two radially extending tabs disposed on the distal end of the dilator hub having a distal surface and a proximal surface;

two axially aligned pins disposed on the distal surface of the tabs; and an introducer hub having a distal end and a proximal end, the introducer hub disposed at the proximal end of the introducer sheath and defining an introducer conduit therethrough, a cylindrical recess at the proximal end and two circumferentially extending slots for rotatably receiving the tabs that terminate in closed ends defining a first stop to inhibit a rotational disengagement of the tabs from the slots in a first circumferential direction, the slots are sized so as to provide an interference fit between the introducer hub and the tabs defining a second stop to inhibit a rotational disengagement of the tabs from the slots in a second circumferential direction, and the introducer hub further defining projections sized so as to inhibit an axial disengagement of the tabs from the slots.

21. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough and a cylindrical recess at the proximal end;

two axially aligned pins disposed within the cylindrical recess at the proximal end of the introducer hub;

a dilator comprising an elongated tubular element having a distal end and a proximal end, the dilator defining a longitudinal dilator conduit, the dilator having a tapered distal portion, the dilator being receivable through the introducer conduit so that the tapered distal portion of the dilator extends beyond the distal end of the introducer sheath; and a dilator hub having a distal end and a proximal end, the dilator hub disposed at the proximal end of the dilator and defining a dilator conduit therethrough and two circumferentially extending slots for rotatably receiving the pins that terminate in closed ends defining a first stop to inhibit a rotational disengagement of the pins from the slots in a first circumferential direction, the slots are sized so as to provide an interference fit between the dilator hub and the pins defining a second stop to inhibit a rotational disengagement of the pins from the slots in a second circumferential direction, and the dilator hub further defining projections sized so as to inhibit an axial disengagement of the pins from the slots.

22. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough and a cylindrical recess at the proximal end;

an obturator comprising an elongated tubular element having a distal end and a proximal end, the obturator defining a longitudinal obturator conduit, the obturator being receivable through the introducer conduit;

an obturator hub having a distal end and a proximal end, the obturator hub disposed at the proximal end of the obturator and further defining an obturator conduit therethrough;

two radially extending tabs disposed on the distal end of the obturator hub;

two circumferentially extending projections disposed within the cylindrical recess at the proximal end of the introducer hub so as to form two slots for rotatably receiving the tabs and that terminate in end walls defining a first stop to inhibit a rotational disengagement of the tabs from the slots in a first circumferential direction, the projections further inhibit an axial disengagement of the tabs from the slots; and two protuberances disposed within the cylindrical recess at the proximal end of the introducer hub, each of the protuberances is sized to provide an interference fit between the protuberance and one of the radially extending tabs so as to define a second stop to inhibit a rotational disengagement of the tabs from the slots in a second circumferential direction.

23. A catheter assembly comprising:
an introducer sheath comprising an elongated tubular element having a distal end and a proximal end, the introducer sheath defining an introducer conduit along a longitudinal axis;
an introducer hub having a distal end and proximal end, the introducer hub disposed at the proximal end of the introducer sheath and further defining an introducer conduit therethrough and a cylindrical recess at the proximal end;
an obturator comprising an elongated tubular element having a distal end and a proximal end, the obturator defining a longitudinal obturator conduit, the obturator being receivable through the introducer conduit;
an obturator hub having a distal end and a proximal end, the obturator hub disposed at the proximal end of the obturator and further defining an obturator conduit therethrough;
two radially extending tabs disposed on the distal end of the obturator hub having a distal surface and a proximal surface, and defining a plurality of indentations on the distal and proximal surfaces of the tabs;
two circumferentially extending projections disposed within the cylindrical recess at the proximal end of the introducer hub so as to form two circumferentially extending slots for rotatably receiving the tabs that terminate in end walls defining a first stop to inhibit a rotational disengagement of the tabs from the slots in a first circumferential direction, the projections further inhibit an axial disengagement of the tabs from the slots; and
a plurality of protuberances extending circumferentially along the projections and circumferentially along a surface of the cylindrical recess in the proximal end of the introducer hub such that the two slots are complementary to the tabs, the protuberances are sized so as to provide an interference fit between the protuberances and the tabs defining a second stop to inhibit a rotational disengagement of the tabs from the slots in a second circumferential direction.

24. A catheter assembly comprising:
an introducer sheath comprising an elongated tubular element having a distal end and a proximal end, the introducer sheath defining an introducer conduit along a longitudinal axis;
an obturator comprising an elongated tubular element having a distal end and a proximal end, the obturator defining a longitudinal obturator conduit, the obturator being receivable through the introducer conduit;
an obturator hub having a distal end and a proximal end, the obturator hub disposed at the proximal end of the obturator and further defining an obturator conduit therethrough;
two radially extending tabs disposed on the distal end of the obturator hub having a distal surface and a proximal surface;
two axially aligned pins disposed on the distal surface of the tabs; and
an introducer hub having a distal end and a proximal end, the introducer hub disposed at the proximal end of the introducer sheath and defining an introducer conduit therethrough, a cylindrical recess at the proximal end and two circumferentially extending slots for rotatably receiving the tabs that terminate in closed ends defining a first stop to inhibit a rotational disengagement of the tabs from the slots in a first circumferential direction, the slots are sized so as to provide an interference fit between the introducer hub and the tabs defining a second stop to inhibit a rotational disengagement of the tabs from the slots in a second circumferential direction, and the introducer hub further defining projections sized so as to inhibit an axial disengagement of the tabs from the slots.

25. A catheter assembly comprising:
an introducer sheath comprising an elongated tubular element having a distal end and a proximal end, the introducer sheath defining an introducer conduit along a longitudinal axis;
an introducer hub having a distal end and proximal end, the introducer hub disposed at the proximal end of the introducer sheath and further defining an introducer conduit therethrough; and a cylindrical recess at the proximal end;
two axially aligned pins disposed with the cylindrical recess at the proximal end of the introducer hub;
an obturator comprising an elongated tubular element having a distal end and a proximal end, the obturator defining a longitudinal obturator conduit, the obturator being receivable through the introducer conduit; and
an obturator hub having a distal end and a proximal end, the obturator hub disposed at the proximal end of the obturator and defining a obturator conduit therethrough and two circumferentially extending slots for rotatably receiving the pins that terminate in closed ends defining a first stop to inhibit a rotational disengagement of the pins from the slots in a first circumferential direction, the slots are sized so as to provide an interference fit between the obturator hub and the pins defining a second stop to inhibit a rotational disengagement of the pins from the slots in a second circumferential direction, and the obturator hub further defining projections sized so as to inhibit an axial disengagement of the pins from the slots.

26. A catheter assembly comprising:
an introducer sheath comprising an elongated tubular element having a distal end and a proximal end, the introducer sheath defining an introducer conduit along a longitudinal axis;
an introducer hub having a distal end and proximal end, the introducer hub disposed at the proximal end of the introducer sheath and further defining an introducer conduit therethrough and a cylindrical recess at the proximal end;
a sleeve comprising an elongated tubular element having a distal end and a proximal end;
a sleeve hub having a distal end and a proximal end, the sleeve hub disposed at the proximal end of the sleeve;
two radially extending tabs disposed on the distal end of the sleeve hub;

two circumferentially extending projections disposed within the cylindrical recess at the proximal end of the introducer hub so as to form two slots for rotatably receiving the tabs and that terminate in end walls defining a first stop to inhibit a rotational disengagement of the tabs from the slots in a first circumferential direction, the projections further inhibit an axial disengagement of the tabs from the slots; and two protuberances disposed within the cylindrical recess at the proximal end of the introducer hub, each of the protuberances is sized to provide an interference fit between the protuberance and one of the radially extending tabs so as to define a second stop to inhibit a rotational disengagement of the tabs from the slots in a second circumferential direction.

27. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough and a cylindrical recess at the proximal end;

a sleeve comprising an elongated tubular element having a distal end and a proximal end;

a sleeve hub having a distal end and a proximal end, the sleeve hub disposed at the proximal end of the sleeve;

two radially extending tabs disposed on the distal end of the sleeve hub having a distal surface and a proximal surface, and defining a plurality of indentations on the distal and proximal surfaces of the tabs;

two circumferentially extending projections disposed within the cylindrical recess at the proximal end of the introducer hub so as to form two circumferentially extending slots for rotatably receiving the tabs that terminate in end walls defining a first stop to inhibit a rotational disengagement of the tabs from the slots in a first circumferential direction, the projections further inhibit an axial disengagement of the tabs from the slots; and a plurality of protuberances extending circumferentially along the projections and circumferentially along a surface of the cylindrical recess in the proximal end of the introducer hub such that the two slots are complementary to the tabs, the protuberances are sized so as to provide an interference fit between the protuberances and the tabs defining a second stop to inhibit a rotational disengagement of the tabs from the slots in a second circumferential direction.

28. A catheter assembly comprising:

an introducer sheath comprising an elongated tubular element having a distal end and a proximal end, the introducer sheath defining an introducer conduit along a longitudinal axis;

a sleeve comprising an elongated tubular element having a distal end and a proximal end;

a sleeve hub having a distal end and a proximal end, the sleeve hub disposed at the proximal end of the sleeve;

two radially extending tabs disposed on the distal end of the sleeve hub having a distal surface and a proximal surface;

two axially aligned pins disposed on the distal surface of the tabs; and an introducer hub having a distal end and a proximal end, the introducer hub disposed at the proximal end of the introducer sheath and defining an introducer conduit therethrough, a cylindrical recess at the proximal end and two circumferentially extending slots for rotatably receiving the tabs that terminate in closed ends defining a first stop to inhibit a rotational disengagement of the tabs from the slots in a first circumferential direction, the slots are sized so as to provide an interference fit between the introducer hub and the tabs defining a second stop to inhibit a rotational disengagement of the tabs from the slots in a second circumferential direction, and the introducer hub further defining projections sized so as to inhibit an axial disengagement of the tabs from the slots.

29. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough; and a cylindrical recess at the proximal end;

two axially aligned pins disposed with the cylindrical recess at the proximal end of the introducer hub;

a sleeve comprising an elongated tubular element having a distal end and a proximal end; and a sleeve hub having a distal end and a proximal end, the sleeve hub disposed at the proximal end of the sleeve and defining and two circumferentially extending slots for rotatably receiving the pins that terminate in closed ends defining a first stop to inhibit a rotational disengagement of the pins from the slots in a first circumferential direction, the slots are sized so as to provide an interference fit between the sleeve hub and the pins defining a second stop to inhibit a rotational disengagement of the pins from the slots in a second circumferential direction, and the sleeve hub further defining projections sized so as to inhibit an axial disengagement of the pins from the slots.

30. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough and a cylindrical recess at the proximal end;

a Tuohy-Borst connector comprising an elongated tubular element having a distal end and a proximal end, the Tuohy-Borst connector defining a longitudinal connector conduit;

a Tuohy-Borst hub having a distal end and a proximal end, the Tuohy-Borst hub disposed at the proximal end of the Tuohy-Borst connector and further defining a connector conduit therethrough;

two radially extending tabs disposed on the distal end of the Tuohy-Borst hub;

two circumferentially extending projections disposed within the cylindrical recess at the proximal end of the introducer hub so as to form two slots for rotatably receiving the tabs and that terminate in end walls defining a first stop to inhibit a rotational disengagement of the tabs from the slots in a first circumferential direction, the projections further inhibit an axial disengagement of the tabs from the slots; and two protuberances disposed within the cylindrical recess at the proximal end of the introducer hub, each of the protuberances is sized to provide an interference fit between the protuberance and one of the radially extending tabs so as to define a second stop to inhibit a rotational disengagement of the tabs from the slots in a second circumferential direction.

31. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough and a cylindrical recess at the proximal end;

a Tuohy-Borst connector comprising an elongated tubular element having a distal end and a proximal end, the Tuohy-Borst connector defining a longitudinal connector conduit;

a Tuohy-Borst hub having a distal end and a proximal end, the Tuohy-Borst hub disposed at the proximal end of the Tuohy-Borst connector and further defining a connector conduit therethrough;

two radially extending tabs disposed on the distal end of the Tuohy-Borst hub having a distal surface and a proximal surface, and defining a plurality of indentations on the distal and proximal surfaces of the tabs;

two circumferentially extending projections disposed within the cylindrical recess at the proximal end of the introducer hub so as to form two circumferentially extending slots for rotatably receiving the tabs that terminate in end walls defining a first stop to inhibit a rotational disengagement of the tabs from the slots in a first circumferential direction, the projections further inhibit an axial disengagement of the tabs from the slots; and a plurality of protuberances extending circumferentially along the projections and circumferentially along a surface of the cylindrical recess in the proximal end of the introducer hub such that the two slots are complementary to the tabs, the protuberances are sized so as to provide an interference fit between the protuberances and the tabs defining a second stop to inhibit a rotational disengagement of the tabs from the slots in a second circumferential direction.

32. A catheter assembly comprising:

an introducer sheath comprising an elongated tubular element having a distal end and a proximal end, the introducer sheath defining an introducer conduit along a longitudinal axis;

a Tuohy-Borst connector comprising an elongated tubular element having a distal end and a proximal end, the Tuohy-Borst connector defining a longitudinal connector conduit;

a Tuohy-Borst hub having a distal end and a proximal end, the Tuohy-Borst hub disposed at the proximal end of the Tuohy-Borst connector and further defining a connector conduit therethrough;

two radially extending tabs disposed on the distal end of the Tuohy-Borst hub having a distal surface and a proximal surface;

two axially aligned pins disposed on the distal surface of the tabs; and an introducer hub having a distal end and a proximal end, the introducer hub disposed at the proximal end of the introducer sheath and defining an introducer conduit therethrough, a cylindrical recess at the proximal end and two circumferentially extending slots for rotatably receiving the tabs that terminate in closed ends defining a first stop to inhibit a rotational disengagement of the tabs from the slots in a first circumferential direction, the slots are sized so as to provide an interference fit between the introducer hub and the tabs defining a second stop to inhibit a rotational disengagement of the tabs from the slots in a second circumferential direction, and the introducer hub further defining projections sized so as to inhibit an axial disengagement of the tabs from the slots.

33. A catheter assembly comprising:

an introducer sheath comprising an elongated tubular element having a distal end and a proximal end, the introducer sheath defining an introducer conduit along a longitudinal axis;

an introducer hub having a distal end and proximal end, the introducer hub disposed at the proximal end of the introducer sheath and further defining an introducer conduit therethrough; and a cylindrical recess at the proximal end;

two axially aligned pins disposed with the cylindrical recess at the proximal end of the introducer hub;

a Tuohy-Borst connector comprising an elongated tubular element having a distal end and a proximal end, the Tuohy-Borst connector defining a longitudinal connector conduit; and a Tuohy-Borst hub having a distal end and a proximal end, the Tuohy-Borst hub disposed at the proximal end of the dilator and defining a connector conduit therethrough and two circumferentially extending slots for rotatably receiving the pins that terminate in closed ends defining a first stop to inhibit a rotational disengagement of the pins from the slots in a first circumferential direction, the slots are sized so as to provide an interference fit between the Tuohy-Borst hub and the pins defining a second stop to inhibit a rotational disengagement of the pins from the slots in a second circumferential direction, and the Tuohy-Borst hub further defining projections sized so as to inhibit an axial disengagement of the pins from the slots.

34. A catheter assembly comprising:

a first catheter element having a proximal end and a distal end;

a first catheter element hub having a distal end and a proximal end, the first catheter element hub disposed at the proximal end of the first catheter element;

two radially extending tabs disposed on the distal end of the first catheter element hub;

a second catheter element having a proximal end and a distal end;

a second catheter element hub having a distal end and a proximal end, the second catheter element hub disposed at the proximal end of the second catheter element and further defining a cylindrical recess at the proximal end;

two circumferentially extending projections disposed within the cylindrical recess at the proximal end of the second catheter element hub so as to form two slots for rotatably receiving the tabs and that terminate in end walls defining a first stop to inhibit a rotational disengagement of the tabs from the slots in the first circumferential direction, the projections further inhibit an axial disengagement of the tabs from the slots; and two protuberances disposed within the cylindrical recess at the proximal end of the second catheter element hub, each of the protuberances is sized to provide an interference fit between the protuberance and one of the radially extending tabs so as to define a second stop to inhibit a rotational disengagement of the tabs from the slots in a second circumferential direction.

35. The catheter assembly defined in claim 34 wherein the second catheter element comprises an introducer sheath.

36. The catheter assembly defined in claim 35 wherein the first catheter element comprises a dilator.

37. The catheter assembly defined in claim 35 wherein the first catheter element comprises an obturator.

38. The catheter assembly defined in claim 35 wherein the first catheter element comprises a sleeve.

39. The catheter assembly defined in claim 35 wherein the first catheter element comprises a Tuohy-Borst connector.

40. A catheter assembly comprising:

a first catheter element having a proximal end and a distal end;

a first catheter element hub that having a distal end and a proximal end, the first catheter element hub disposed at the proximal end of the first catheter element;

two radially extending tabs disposed on the distal end of the first catheter element hub, the tabs having a distal surface and proximal surface and defining a plurality of indentations on the distal and proximal surfaces of the tabs;

a second catheter element having a proximal end and a distal end;

a second catheter element hub having a distal end and a proximal end, the second catheter element hub disposed at the proximal end of the second catheter element and further defining a cylindrical recess at the proximal end;

two circumferentially extending projections disposed within the cylindrical recess at the proximal end of the second catheter element hub so as to form two circumferentially extending slots for rotatably receiving the tabs that terminate in end walls defining a first stop to inhibit a rotational disengagement of the tabs from the slots in a first circumferential direction, the projections further inhibit an axial disengagement of the tabs from the slots; and a plurality of protuberances extending circumferentially along the projections and circumferentially along a surface of the cylindrical recess in the proximal end of the second catheter element hub such that the two slots are complementary to the tabs, the protuberances are sized so as to provide an interference fit between the protuberances and the tabs defining a second stop to inhibit a rotational disengagement of the tabs from the slots in a second circumferential direction.

41. The catheter assembly defined in claim 40 wherein the second catheter element comprises an introducer sheath.

42. The catheter assembly defined in claim 41 wherein the first catheter element comprises a dilator.

43. The catheter assembly defined in claim 41 wherein the first catheter element comprises an obturator.

44. The catheter assembly defined in claim 41 wherein the first catheter element comprises a sleeve.

45. The catheter assembly defined in claim 41 wherein the first catheter element comprises a Tuohy-Borst connector.

46. A catheter assembly comprising:

a first catheter element having a proximal end and a distal end;

a first catheter element hub being a distal end and a proximal end, the first catheter element hub disposed at the proximal end of the first catheter element;

two radially extending tabs disposed on the distal end of the first catheter element hub, the tabs having a distal surface and a proximal surface;

two axially aligned pins disposed on the distal surface of the tabs;

a second catheter element having a proximal end and a distal end; and a second catheter element hub having a distal end and a proximal end, the second catheter element hub disposed at the proximal end of the second catheter element and defining a cylindrical recess at the proximal end and two circumferentially extending slots for rotatably receiving the tabs that terminate in closed ends defining a first stop to inhibit a rotational disengagement of the tabs from the slots in a first circumferential direction, the slots are sized so as to provide an interference fit between the second catheter element hub and the tabs defining a second stop to inhibit a rotational disengagement of the tabs from the slots in a second circumferential direction, and the second catheter element hub further defining projections sized so as to inhibit an axial disengagement of the tabs from the slots.

47. The catheter assembly defined in claim 46 wherein the second catheter element comprises an introducer sheath.

48. The catheter assembly defined in claim 47 wherein the first catheter element comprises a dilator.

49. The catheter assembly defined in claim 47 wherein the first catheter element comprises an obturator.

50. The catheter assembly defined in claim 47 wherein the first catheter element comprises a sleeve.

51. The catheter assembly defined in claim 47 wherein the first catheter element comprises a Tuohy-Borst connector.

52. A catheter assembly comprising:

a first catheter element having a proximal end and a distal end;

a second catheter element having a proximal end and a distal end;

a second catheter element hub having a proximal end and a distal end, the second catheter element hub disposed at the proximal end of the second catheter element and defining a cylindrical recess at the proximal end;

two axially aligned pins disposed within the cylindrical recess at the proximal end of the second catheter element hub; and a first catheter element hub having a distal end and a proximal end, the first catheter element hub disposed at the proximal end of the first catheter element and defining two circumferentially extending slots for rotatably receiving the pins that terminate in closed ends defining a first stop to inhibit a rotational disengagement of the pins from the slots in a first circumferential direction, the slots are sized so as to provide an interference fit between the first catheter element hub and the pins defining a second stop to inhibit a rotational disengagement of the pins from the slots in a second circumferential direction, and the first catheter element hub further defining projections sized so as to inhibit an axial disengagement of the pins from the slots.

53. The catheter assembly defined in claim 52 wherein the second catheter element comprises an introducer sheath.

54. The catheter assembly defined in claim 53 wherein the first catheter element comprises a dilator.

55. The catheter assembly defined in claim 53 wherein the first catheter element comprises an obturator.

56. The catheter assembly defined in claim 53 wherein the first catheter element comprises a sleeve.

57. The catheter assembly defined in claim 53 wherein the first catheter element comprises a Tuohy-Borst connector.

* * * * *